US011547272B2

(12) United States Patent
Iwane

(10) Patent No.: US 11,547,272 B2
(45) Date of Patent: Jan. 10, 2023

(54) ENDOSCOPE SYSTEM AND METHOD OF OPERATING THE SAME

(71) Applicant: FUJIFILM Corporation, Tokyo (JP)

(72) Inventor: Kosuke Iwane, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 120 days.

(21) Appl. No.: 16/936,529

(22) Filed: Jul. 23, 2020

(65) Prior Publication Data
US 2020/0345225 A1 Nov. 5, 2020

Related U.S. Application Data

(63) Continuation of application No. PCT/JP2019/002775, filed on Jan. 28, 2019.

(30) Foreign Application Priority Data

Jan. 30, 2018 (JP) .............................. JP2018-013266

(51) Int. Cl.
*A61B 1/00* (2006.01)
*A61B 1/045* (2006.01)
(Continued)

(52) U.S. Cl.
CPC ...... *A61B 1/000094* (2022.02); *A61B 1/0005* (2013.01); *A61B 1/00006* (2013.01);
(Continued)

(58) Field of Classification Search
CPC ...... A61B 1/063; A61B 1/3137; A61B 1/0051
See application file for complete search history.

(56) References Cited

U.S. PATENT DOCUMENTS 4,491,865 A * 1/1985 Danna .................. H04N 5/2253
348/E5.025
9,649,018 B2 * 5/2017 Morimoto ............ A61B 1/0646
(Continued)

FOREIGN PATENT DOCUMENTS

JP   H03-032634 A   2/1991
JP   2011-019829 A   2/2011
(Continued)

OTHER PUBLICATIONS

An Office Action; "Decision of Refusal", mailed by the Japanese Patent Office dated May 18, 2021, which corresponds to Japanese Patent Application No. 2019-569098 and is related to U.S. Appl. No. 16/936,529; with English language translation.
(Continued)

*Primary Examiner* — Anh Tuan T Nguyen
*Assistant Examiner* — Jae Woo
(74) *Attorney, Agent, or Firm* — Studebaker & Brackett PC

(57) ABSTRACT

A special observation image is obtained by performing an image pickup of an object to be observed illuminated with special light. Bs-image signals of the special observation image are assigned to brightness signals Y to generate a first observation image for display. Gs-image signals of the special observation image are assigned to brightness signals Y to generate a second observation image for display. The first observation image for display and the second observation image for display are automatically switched and displayed on a monitor.

17 Claims, 15 Drawing Sheets

(51) Int. Cl.
*A61B 1/06* (2006.01)
*A61B 1/313* (2006.01)
*A61B 1/005* (2006.01)

(52) U.S. Cl.
CPC .............. *A61B 1/045* (2013.01); *A61B 1/063* (2013.01); *A61B 1/0684* (2013.01); *A61B 1/3137* (2013.01); *A61B 1/0051* (2013.01)

(56) References Cited

U.S. PATENT DOCUMENTS

| | | | | |
|---|---|---|---|---|
| 9,943,230 | B2* | 4/2018 | Kaku | A61B 1/000094 |
| 2005/0059894 | A1* | 3/2005 | Zeng | A61B 5/0075 |
| | | | | 600/476 |
| 2010/0063352 | A1* | 3/2010 | Matsuura | H04N 5/23248 |
| | | | | 600/109 |
| 2012/0197077 | A1* | 8/2012 | Kaku | A61B 1/0653 |
| | | | | 600/109 |
| 2013/0006109 | A1* | 1/2013 | Takei | A61B 1/043 |
| | | | | 600/432 |
| 2014/0221745 | A1* | 8/2014 | Yamaguchi | H04N 9/0451 |
| | | | | 600/109 |
| 2014/0340497 | A1* | 11/2014 | Shigeta | A61B 1/043 |
| | | | | 348/71 |
| 2016/0089010 | A1* | 3/2016 | Aoyama | A61B 1/0005 |
| | | | | 348/70 |
| 2018/0289240 | A1 | 10/2018 | Aoyama | |
| 2019/0008362 | A1 | 1/2019 | Kamon | |
| 2020/0260942 | A1* | 8/2020 | Kubo | A61B 1/0655 |
| 2020/0268231 | A1* | 8/2020 | Kubo | A61B 1/0684 |
| 2021/0400181 | A1* | 12/2021 | Taniguchi | H04N 5/2352 |

FOREIGN PATENT DOCUMENTS

| | | |
|---|---|---|
| JP | 2012152414 A | 8/2012 |
| JP | 2016-067775 A | 5/2016 |
| JP | 2016067780 A | 5/2016 |
| JP | 2017060682 A | 3/2017 |
| JP | 2017-164021 A | 9/2017 |
| WO | 2017/110334 A1 | 6/2017 |

OTHER PUBLICATIONS

An Office Action; "Notice of Reasons for Refusal", mailed by the Japanese Patent Office dated May 31, 2022, which corresponds to Japanese Patent Application No. 2021-116356 and is related to U.S. Appl. No. 16/936,529; with English language translation.

International Search Report issued in PCT/JP2019/002775; dated Mar. 26, 2019.

International Preliminary Report on Patentability and Written Opinion issued in PCT/JP2019/002775; dated Aug. 4, 2020.

An Office Action; "Notice of Reasons for Refusal", mailed by the Japanese Patent Office dated Feb. 24, 2021, which corresponds to Japanese Patent Application No. 2019-569098 and is related to U.S. Appl. No. 16/936,529; with English language translation.

* cited by examiner

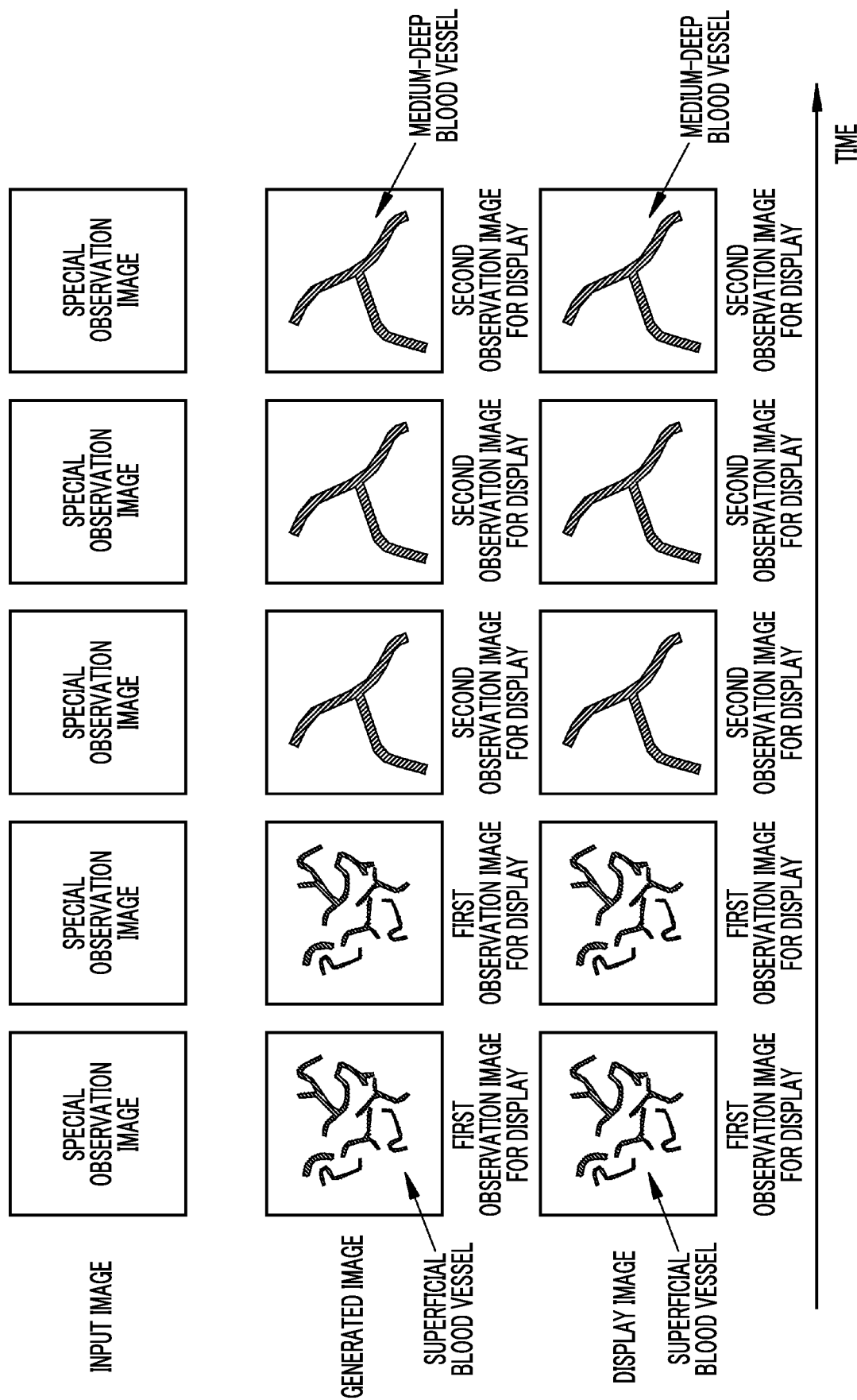

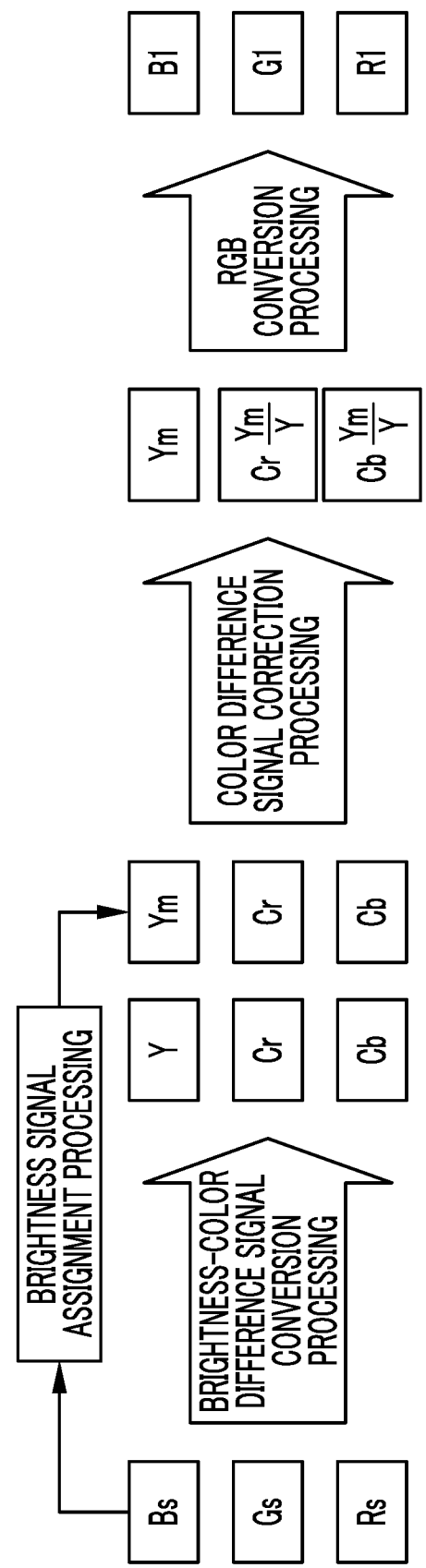

FIG. 9
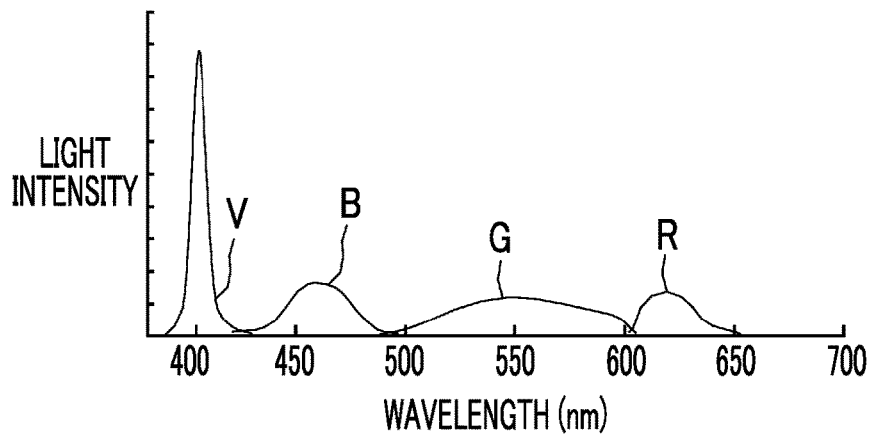
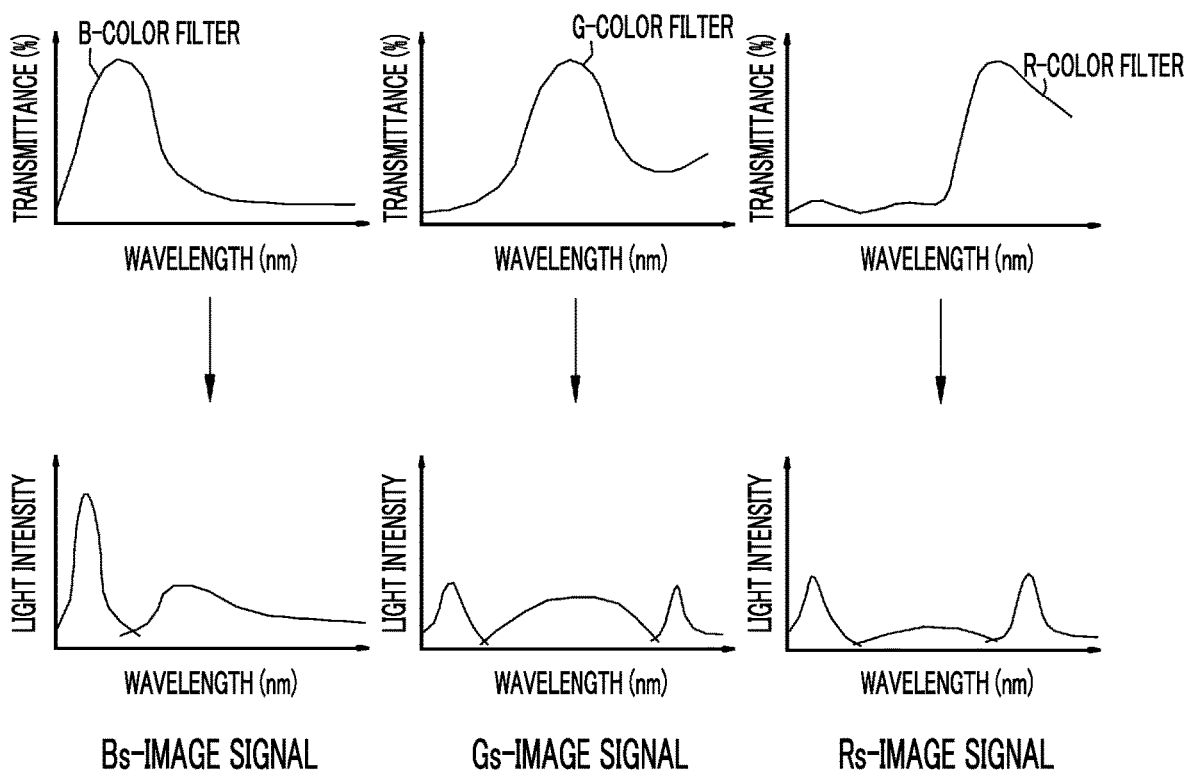

ENDOSCOPE SYSTEM AND METHOD OF OPERATING THE SAME

CROSS-REFERENCE TO RELATED APPLICATIONS

This application is a Continuation of PCT International Application No. PCT/JP2019/002775 filed on 28 Jan. 2019, which claims priority under 35 U.S.C. § 119(a) to Japanese Patent Application No. 2018-013266 filed on 30 Jan. 2018. The above application is hereby expressly incorporated by reference, in its entirety, into the present application.

BACKGROUND OF THE INVENTION

1. Field of the Invention

The present invention relates to an endoscope system and a method of operating the endoscope system that automatically switch and display a plurality of observation images.

2. Description of the Related Art

In recent years, an endoscope system comprising a light source device, an endoscope, and a processor device has been widely used in a medical field. In the endoscope system, an object to be observed is irradiated with illumination light from an endoscope, and the image of the object to be observed is displayed on a monitor on the basis of RGB image signals that are obtained in a case where the image of the object to be observed, which is being illuminated with the illumination light, is picked up by an image pickup element of the endoscope.

In recent years, a plurality of observation images having different display contents have been simultaneously displayed or switched and displayed on a monitor according to the purpose of diagnosis. A plurality of images of which the thicknesses and depths of blood vessels are different from each other are switched and displayed in, for example, JP2017-060682A. Further, in JP2016-067780A, an image corresponding to violet light V and an image corresponding to blue light B are acquired by illumination using the violet light V and the blue light B that are being switched, the image corresponding to the violet light V is assigned to brightness signals in a case where extremely superficial blood vessels are to be emphasized, and the image corresponding to the blue light B is assigned to brightness signals in a case where superficial blood vessels are to be emphasized.

SUMMARY OF THE INVENTION

In a case where a plurality of observation images are to be switched and displayed on the monitor as described above, it is preferable that processing and operations involved in switching the images, such as processing to be performed on the observation images, are reduced as much as possible. In this regard, processing for emphasizing blood vessels having different thicknesses and depths is required in JP2017-060682A. For this reason, the load of image processing involved in switching the images is increased. Further, since a plurality of kinds of illumination light are switched in JP2016-067780A, a processor device needs to be synchronized in accordance with the switching of the illumination light. For this reason, the load of processing in the processor device is increased.

An object of the invention is to provide an endoscope system and a method of operating the endoscope system that can reduce processing and operations involved in switching a plurality of observation images as much as possible in a case where the observation images are to be automatically switched and displayed.

An endoscope system according to an aspect of the invention comprises an image acquisition unit, an observation-image-for-display processing unit, and a display control unit. The image acquisition unit acquires an observation image. In a case where the observation-image-for-display processing unit generates an observation image for display including a brightness signal on the basis of the observation image, the observation-image-for-display processing unit assigns a first color signal of the observation image to the brightness signal to generate a first observation image for display and assigns a second color signal of the observation image to the brightness signal to generate a second observation image for display. The display control unit causes a display unit to automatically switch and display the first observation image for display and the second observation image for display.

It is preferable that the observation-image-for-display processing unit removes a component of the second color signal of the observation image from the first color signal of the observation image by first arithmetic processing based on the first color signal of the observation image and the second color signal of the observation image and assigns the first color signal of the observation image, which has been subjected to the first arithmetic processing, to the brightness signal to generate the first observation image for display. It is preferable that the observation-image-for-display processing unit removes a component of the first color signal of the observation image from the second color signal of the observation image by second arithmetic processing based on the first color signal of the observation image and the second color signal of the observation image and assigns the second color signal of the observation image, which has been subjected to the second arithmetic processing, to the brightness signal to generate the second observation image for display.

It is preferable that the observation image is a special observation image obtained from image pickup of an object to be observed illuminated with special light including blue light or violet light of which a wavelength range is narrowed, green light, and red light. It is preferable that the violet light has a central wavelength in a range of 405±10 nm. It is preferable that the first color signal is a blue color signal and the second color signal is a green color signal.

It is preferable that first layer blood vessels are emphasized in the first observation image for display and second layer blood vessels present at a position deeper than the first layer blood vessels are emphasized in the second observation image for display. It is preferable that the first layer blood vessels are superficial blood vessels and the second layer blood vessels are medium-deep blood vessels. It is preferable that the display control unit causes the first observation image for display and the second observation image for display to be displayed while the first observation image for display and the second observation image for display are switched at an interval of two or more frames.

A method of operating an endoscope system according to another aspect of the invention comprises an image acquisition step, an image generation step, and a display step. In the image acquisition step, an image acquisition unit acquires an observation image. In the image generation step, an observation-image-for-display processing unit generates an observation image for display including a brightness signal on the basis of the observation image, assigns a first color signal of the observation image to the brightness signal to generate a first observation image for display, and assigns a second color signal of the observation image to the brightness signal to generate a second observation image for display. In the display step, a display control unit causes a display unit to automatically switch and display the first observation image for display and the second observation image for display.

According to the invention, it is possible to reduce processing and operations involved in switching a plurality of observation images as much as possible in a case where the observation images are to be automatically switched and displayed.

BRIEF DESCRIPTION OF THE DRAWINGS

FIG. 6A is a diagram illustrating that any one of a first observation image for display or a second observation image for display is generated from a special observation image of one frame and the generated observation image for display is displayed.

FIG. 7 is a diagram illustrating first-observation-image-for-display generation processing.

FIG. 9 is a diagram illustrating the spectrum of special light, the reflectivity of an object to be observed, and a relationship between the color filters of the image pickup sensor and a Bs-image signal, a Gs-image signal, and a Rs-image signal.

DESCRIPTION OF THE PREFERRED EMBODIMENTS

First Embodiment

Figure 1:
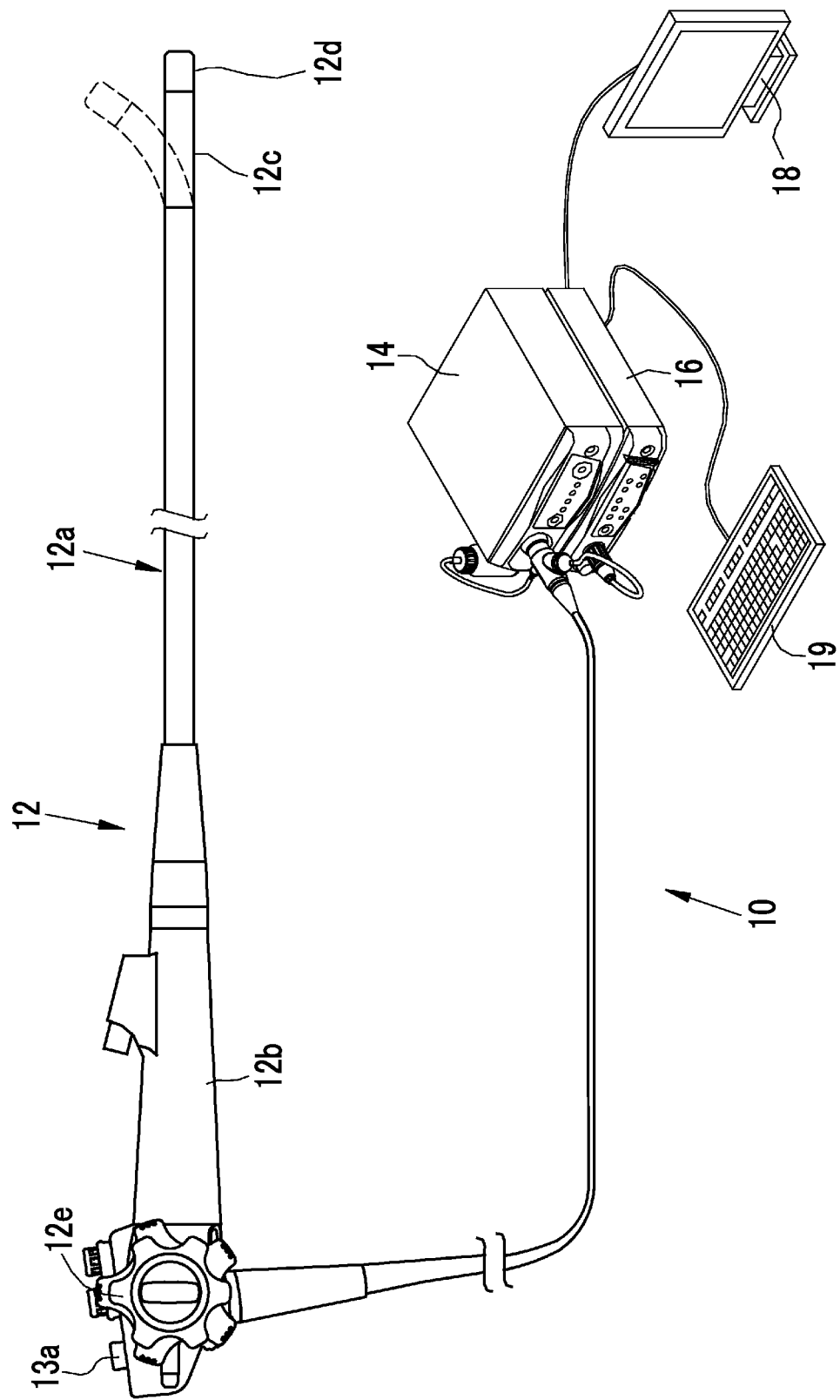
FIG. 1 is a diagram showing the appearance of an endoscope system according to a first embodiment.

As shown in FIG. 1, an endoscope system 10 according to a first embodiment includes an endoscope 12, a light source device 14, a processor device 16, a monitor 18, and a console 19. The endoscope 12 is optically connected to the light source device 14, and is electrically connected to the processor device 16. The endoscope 12 includes an insertion part 12a that is to be inserted into an object to be examined, an operation part 12b that is provided at the proximal end portion of the insertion part 12a, and a bendable part 12c and a distal end part 12d that are provided on the distal end side of the insertion part 12a. In a case where angle knobs 12e of the operation part 12b are operated, the bendable part 12c is operated to be bent. As the bendable part 12c is operated to be bent, the distal end part 12d faces in a desired direction. The console 19 includes a mouse and the like in addition to a keyboard shown in FIG. 1.

Further, the operation part 12b is provided with a mode changeover SW 13a in addition to the angle knobs 12e. The mode changeover SW 13a is used for an operation for switching a normal light observation mode, a special light observation mode, and a multi-observation mode. The normal light observation mode is a mode where a normal observation image is displayed on the monitor 18. The special light observation mode is a mode where a special observation image in which blood vessels positioned at a specific depth are emphasized is displayed on the monitor 18. The multi-observation mode is a mode where a first observation image for display in which superficial blood vessels (first layer blood vessels) are emphasized and a second observation image for display in which medium-deep blood vessels (second layer blood vessels) are emphasized are generated from the special observation image and the first observation image for display and the second observation image for display are automatically switched and displayed on the monitor 18. A foot switch may be used as a mode switching unit, which is used to switch a mode, other than the mode changeover SW 13a. Further, in the multi-observation mode, the first observation image for display or the second observation image for display may be generated from the normal observation image instead of the special observation image.

The processor device 16 is electrically connected to the monitor 18 and the console 19. The monitor 18 outputs and displays image information and the like. The console 19 functions as a user interface (UI) that receives an input operation, such as function settings. An external recording unit (not shown), which records image information and the like, may be connected to the processor device 16.

Figure 2:
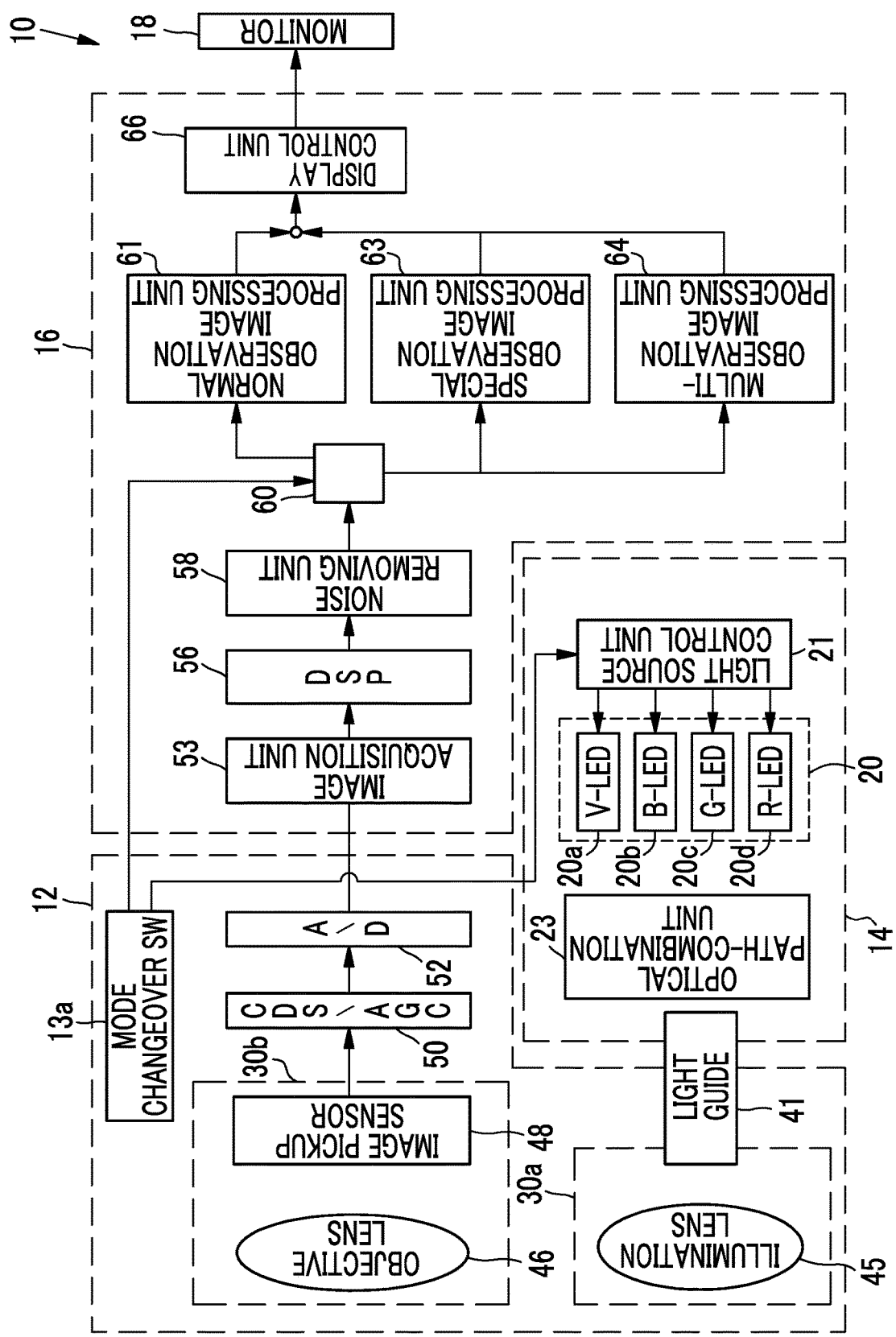
FIG. 2 is a block diagram showing the functions of the endoscope system according to the first embodiment.

As shown in FIG. 2, the light source device 14 includes a light source unit 20, a light source control unit 21, and an optical path-combination unit 23. The light source unit 20 includes a violet light emitting diode (V-LED) 20a, a blue light emitting diode (B-LED) 20b, a green light emitting diode (G-LED) 20c, and a red light emitting diode (R-LED) 20d. The light source control unit 21 controls the drive of the LEDs 20a to 20d. The optical path-combination unit 23 combines the optical paths of four kinds of color light that are emitted from the four color LEDs 20a to 20d. The inside of an object to be examined is irradiated with the pieces of light, which are combined by the optical path-combination unit 23, through a light guide 41 inserted into the insertion part 12a and an illumination lens 45. Other semiconductor light sources, such as a laser diode (LD), may be used instead of the LED.

Figure 3:
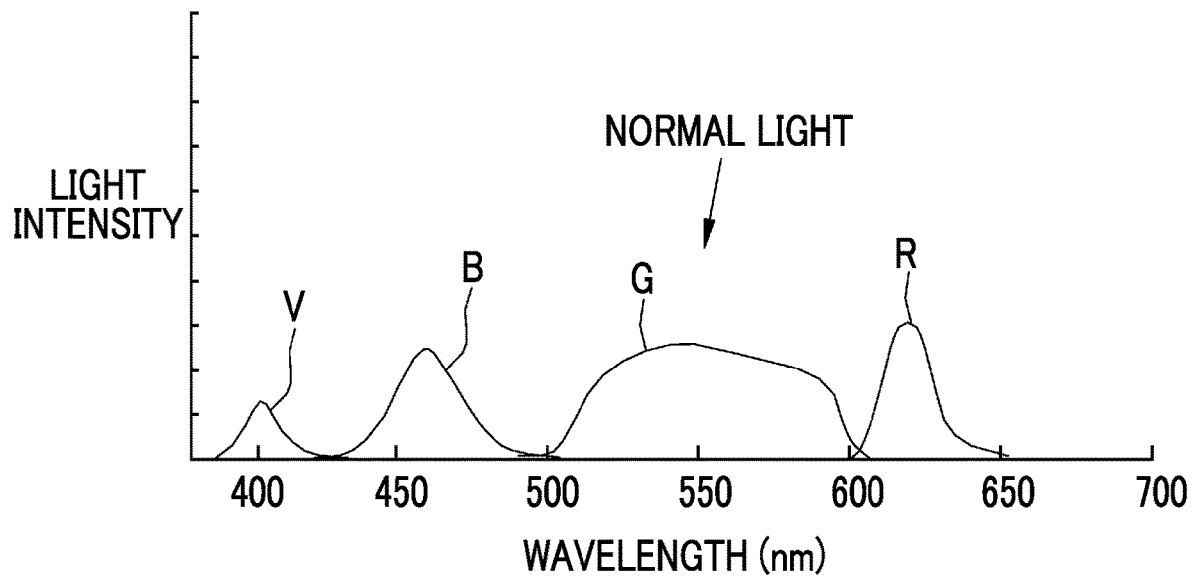
FIG. 3 is a graph showing the emission spectrum of normal light of the first embodiment.

As shown in FIG. 3, the V-LED 20a generates violet light V of which the central wavelength is in the range of 405±10 nm and the wavelength range is in the range of 380 to 420 nm. The B-LED 20b generates blue light B of which the central wavelength is in the range of 460±10 nm and the wavelength range is in the range of 420 to 500 nm. The G-LED 20c generates green light G of which the wavelength range is in the range of 480 to 600 nm. The R-LED 20d generates red light R of which the central wavelength is in the range of 620 to 630 nm and the wavelength range is in the range of 600 to 650 nm. It is preferable that the wavelength range of violet light among the above-mentioned four kinds of color light is narrowed like a wavelength range of 380 to 420 nm.

The light source control unit 21 performs control to turn on the V-LED 20a, the B-LED 20b, the G-LED 20c, and the R-LED 20d in all observation modes. Further, the light source control unit 21 controls the respective LEDs 20a to 20d so that normal light (see FIG. 3) of which the light intensity ratios of violet light V, blue light B, green light G, and red light R are Vc:Bc:Gc:Rc is emitted in the normal light observation mode. In this specification, the light intensity ratios include a case where the ratio of at least one semiconductor light source is 0 (zero). Accordingly, the light intensity ratios include a case where any one or two or more of the respective semiconductor light sources are not turned on. For example, even though only one semiconductor light source is turned on and the other three semiconductor light sources are not turned on as in a case where the light intensity ratios of violet light V, blue light B, green light G, and red light R are 1:0:0:0, it is regarded that the light source unit 20 has light intensity ratios.

Figure 4:
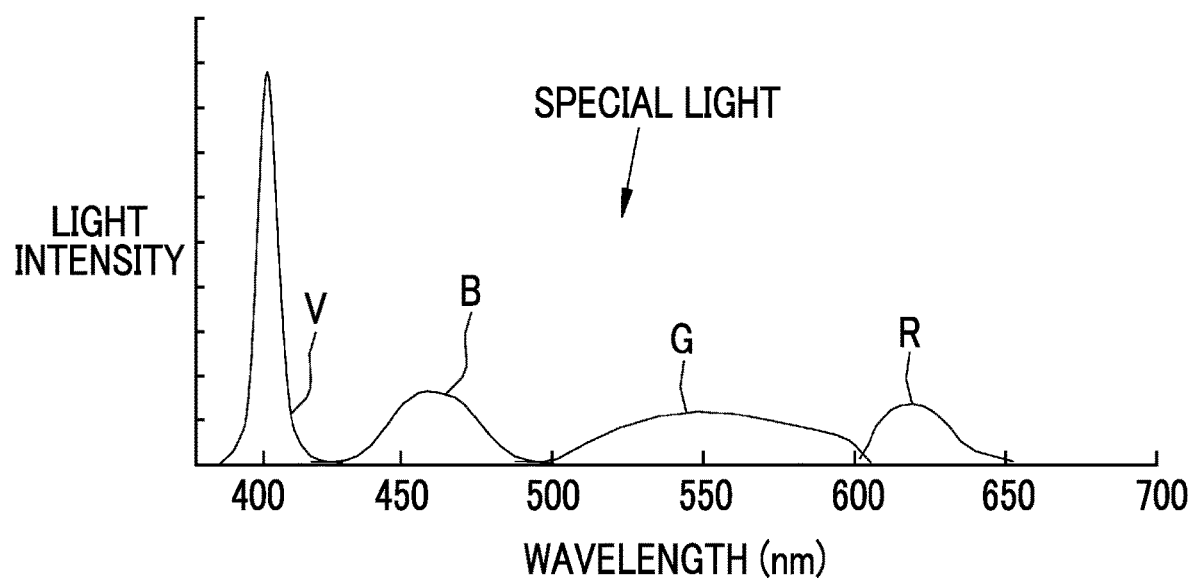
FIG. 4 is a graph showing the emission spectrum of special light of the first embodiment.

Furthermore, the light source control unit 21 controls the respective LEDs 20a to 20d so that special light of which the light intensity ratios of violet light V, blue light B, green light G, and red light R are Vs:Bs:Gs:Rs is emitted in the special light observation mode or the multi-observation mode. It is preferable that the special light is illumination light for emphasizing blood vessels positioned at a specific depth. For example, in a case where superficial blood vessels are to be emphasized as the blood vessels positioned at a specific depth, it is preferable that the special light has a peak in the wavelength range of 400 nm to 440 nm. In this case, the light intensity ratios Vs1:Bs1:Gs1:Rs1 of the special light are set so that the light intensity of violet light V is higher than the light intensity of each of blue light B, green light G, and red light R as shown in FIG. 4 (Vs1>Bs1, Gs1, and Rs1). Further, since the special light includes a first red-light wavelength range like red light R, the special light can accurately reproduce the color of a mucous membrane. Furthermore, since the special light includes a blue-light wavelength range and a green-light wavelength range like violet light V, blue light B, and green light G, the special light can also emphasize various structures, such as glandular structures and unevenness, in addition to the above-mentioned superficial blood vessels.

As shown in FIG. 2, the light guide 41 is built in the endoscope 12 and a universal cord (a cord connecting the endoscope 12 to the light source device 14 and the processor device 16), and transmits the pieces of light, which are combined by the optical path-combination unit 23, to the distal end part 12d of the endoscope 12. A multimode fiber can be used as the light guide 41. For example, a thin fiber cable of which a total diameter of a core diameter of 105 μm, a cladding diameter of 125 μm, and a protective layer forming a covering is in the range of φ 0.3 to 0.5 mm can be used.

The distal end part 12d of the endoscope 12 is provided with an illumination optical system 30a and an image pickup optical system 30b. The illumination optical system 30a includes an illumination lens 45, and an object to be observed is irradiated with light transmitted from the light guide 41 through the illumination lens 45. The image pickup optical system 30b includes an objective lens 46 and an image pickup sensor 48. Light reflected from the object to be observed is incident on the image pickup sensor 48 through the objective lens 46. Accordingly, the reflected image of the object to be observed is formed on the image pickup sensor 48.

The image pickup sensor 48 is a color image pickup sensor, and picks up the reflected image of an object to be examined and outputs image signals. It is preferable that the image pickup sensor 48 is a charge coupled device (CCD) image pickup sensor, a complementary metal-oxide semiconductor (CMOS) image pickup sensor, or the like. The image pickup sensor 48 used in the invention is a color image pickup sensor that is used to obtain RGB image signals corresponding to three colors of R (red), G (green), and B (blue), that is, a so-called RGB image pickup sensor that comprises R-pixels provided with R-color filters, G-pixels provided with G-color filters, and B-pixels provided with B-color filters.

Figure 5:
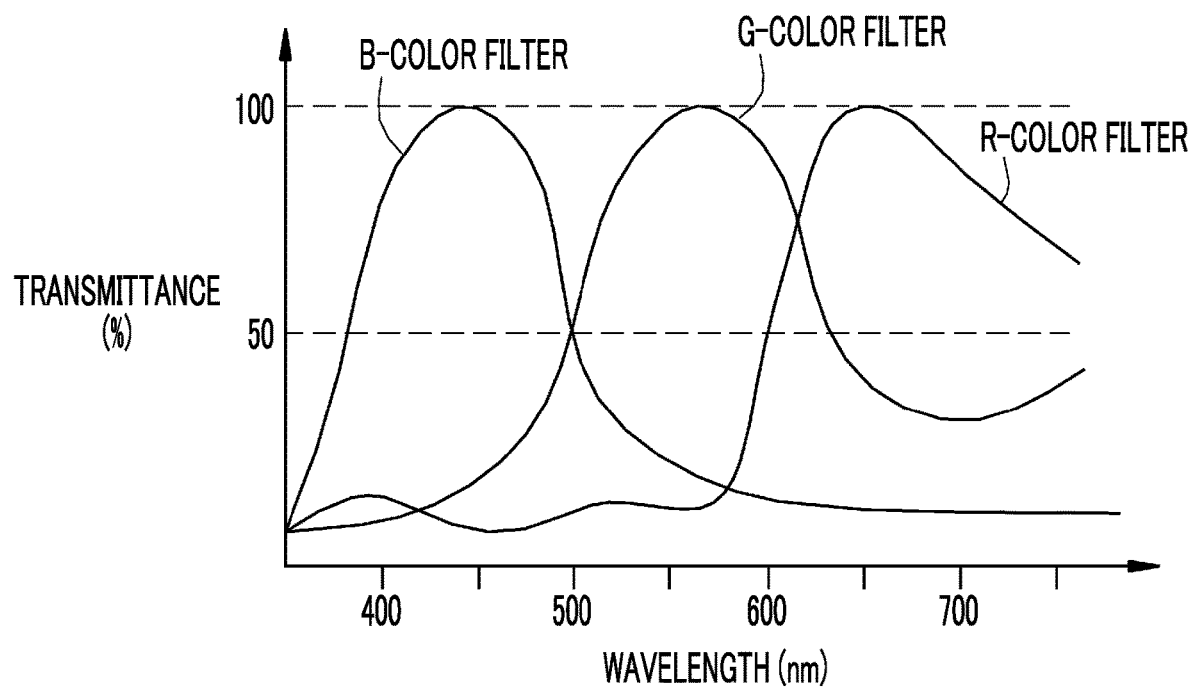
FIG. 5 is a graph showing the transmittance of a B-color filter, a G-color filter, and an R-color filter provided in an image pickup sensor.

As shown in FIG. 5, the R-color filter has a transmittance in a red-light wavelength range of 600 to 700 nm, and has a lower transmittance in a green-light wavelength range and a blue-light wavelength range than that in the red-light wavelength range. That is, the R-pixel has a sensitivity in the red-light wavelength range, and has a slight sensitivity even in the green-light wavelength range and the blue-light wavelength range. The G-color filter has a transmittance in a green-light wavelength range of 500 to 600 nm, and has a slight transmittance even in the red-light wavelength range and the blue-light wavelength range. That is, the G-pixel has a sensitivity in the green-light wavelength range, and has a slight sensitivity even in the red-light wavelength range and the blue-light wavelength range. The B-color filter has a transmittance in a blue-light wavelength range of 400 to 500 nm, and has a slight transmittance even in the green-light wavelength range and the red-light wavelength range. The B-pixel has a sensitivity in the blue-light wavelength range, and has a slight sensitivity even in the green-light wavelength range and the red-light wavelength range.

The image pickup sensor 48 may be a so-called complementary color image pickup sensor, which comprises complementary color filters corresponding to C (cyan), M (magenta), Y (yellow), and G (green), instead of an RGB color image pickup sensor. In a case where a complementary color image pickup sensor is used, image signals corresponding to four colors of C, M, Y, and G are output. Accordingly, the image signals corresponding to four colors of C, M, Y, and G need to be converted into image signals corresponding to three colors of R, G, and B by complementary color-primary color conversion. Further, the image pickup sensor 48 may be a monochrome image pickup sensor that includes no color filter. In this case, since the light source control unit 21 causes blue light B, green light G, and red light R to be emitted in a time-sharing manner, demosaicing needs to be added to the processing of image pickup signals.

The image signals output from the image pickup sensor 48 are transmitted to a CDS/AGC circuit 50. The CDS/AGC circuit 50 performs correlated double sampling (CDS) or auto gain control (AGC) on the image signals that are analog signals. The image signals, which have been transmitted through the CDS/AGC circuit 50, are converted into digital image signals by an analog/digital converter (A/D converter) 52. The digital image signals, which have been subjected to A/D conversion, are input to the processor device 16.

The processor device 16 comprises an image acquisition unit 53, a digital signal processor (DSP) 56, a noise removing unit 58, a signal switching unit 60, a normal observation image processing unit 61, a special observation image processing unit 63, a multi-observation image processing unit 64 (observation-image-for-display processing unit), and a display control unit 66. The image acquisition unit 53 acquires an observation image output from the endoscope 12. The observation image is RGB color image signals. A normal observation image, which consists of Rc-image signals output from the R-pixels of the image pickup sensor 48, Gc-image signals output from the G-pixels of the image pickup sensor 48, and Bc-image signals output from the B-pixels of the image pickup sensor 48, is acquired as an observation image in the normal light observation mode. A special observation image, which consists of Rs-image signals output from the R-pixels of the image pickup sensor 48, Gs-image signals output from the G-pixels of the image pickup sensor 48, and Bs-image signals output from the B-pixels of the image pickup sensor 48, is acquired as an observation image in the special light observation mode or the multi-observation mode.

The DSP 56 performs various kinds of signal processing, such as defect correction processing, offset processing, gain correction processing, linear matrix processing, gamma conversion processing, and demosaicing processing, on the received image signals. Signals of defective pixels of the image pickup sensor 48 are corrected in the defect correction processing. Dark current components are removed from the RGB image signals having been subjected to the defect correction processing in the offset processing, so that an accurate zero level is set. The RGB image signals having been subjected to the offset processing are multiplied by a specific gain in the gain correction processing, so that signal levels are adjusted. The linear matrix processing for improving color reproducibility is performed on the RGB image signals having been subjected to the gain correction processing. After that, lightness or a saturation is adjusted by the gamma conversion processing. The demosaicing processing (also referred to as equalization processing or demosaicing) is performed on the RGB image signals having been subjected to the linear matrix processing, so that signals of colors deficient in each pixel are generated by interpolation. All the pixels are made to have the signals of the respective colors of R, G, and B by this demosaicing processing.

The noise removing unit 58 performs noise removal processing (for example, a moving-average method, median filtering, or the like) on the RGB image signals, which have been subjected to gamma correction and the like by the DSP 56, to remove noise from the RGB image signals. The RGB image signals from which noise has been removed are transmitted to the signal switching unit 60.

In a case where a mode is set to the normal light observation mode by the mode changeover SW 13a, the signal switching unit 60 transmits the RGB image signals to the normal observation image processing unit 61. Further, in a case where a mode is set to the special light observation mode, the signal switching unit 60 transmits the RGB image signals to the special observation image processing unit 63. Furthermore, in a case where a mode is set to the multi-observation mode, the signal switching unit 60 transmits the RGB image signals to the multi-observation image processing unit 64.

The Rc-image signals, the Gc-image signals, and the Bc-image signals, which are obtained in the normal light observation mode, are input to the normal observation image processing unit 61. Image processing for the normal light observation mode is performed on the Rc-image signals, the Gc-image signals, and the Bc-image signals that are input. The image processing for the normal light observation mode includes structure emphasis processing for a normal light observation mode, and the like. The RGB image signals having been subjected to the image processing for the normal light observation mode are input to the display control unit 66 from the normal observation image processing unit 61 as a normal observation image.

The Rs-image signals, the Gs-image signals, and the Bs-image signals, which are obtained in the special light observation mode, are input to the special observation image processing unit 63. Image processing for the special light observation mode is performed on the Rs-image signals, the Gs-image signals, and the Bs-image signals that are input. The image processing for the special light observation mode includes structure emphasis processing for a special light observation mode, and the like. The RGB image signals having been subjected to the image processing for the special light observation mode are input to the display control unit 66 from the special observation image processing unit 63 as a special observation image.

The Rs-image signals, the Gs-image signals, and the Bs-image signals, which are obtained in the multi-observation mode, are input to the multi-observation image processing unit 64. Image processing for the multi-observation mode is performed on the Rs-image signals, the Gs-image signals, and the Bs-image signals that are input. In the image processing for the multi-observation mode, a plurality of observation images for display in which blood vessels positioned at depths different from each other are emphasized are generated from a special observation image of one frame. In this embodiment, the first observation image for display in which superficial blood vessels are emphasized and the second observation image for display in which medium-deep blood vessels are emphasized are generated as the plurality of observation images for display. The details of the image processing for the multi-observation mode will be described later. The first observation image for display and the second observation image for display are input to the display control unit 66 from the multi-observation image processing unit 64.

The display control unit 66 performs control to cause the monitor 18 to display the normal observation image, the special observation image, or the first or second observation image for display that are input from the normal observation image processing unit 61, the special observation image processing unit 63, or the multi-observation image processing unit 64. An image corresponding to each observation mode is displayed on the monitor 18 according to the control of the display control unit 66. The monitor 18 displays the normal observation image in the normal light observation mode. The monitor 18 displays the special observation image in the special light observation mode. In the multi-observation mode, the monitor 18 automatically switches and displays the first observation image for display or the second observation image for display according to a specific display pattern.

For example, in a case where the specific display pattern is to be set to a pattern where the first observation image for display is displayed for two frames and the second observation image for display is displayed for three frames in one display cycle, the following pattern is considered. As shown in FIG. 6A, in a case where special observation images of two frames are input to the multi-observation image processing unit 64 as input images, the multi-observation image processing unit 64 generates first observation images for display for two frames as generated images. The generated first observation images for display for two frames are sequentially displayed on the monitor 18 as display images. After that, in a case where special observation images of three frames are input to the multi-observation image processing unit 64 as input images, the multi-observation image processing unit 64 generates second observation images for display for three frames as generated images. The generated second observation images for display for three frames are sequentially displayed on the monitor 18 as display images.

Figure 6B:
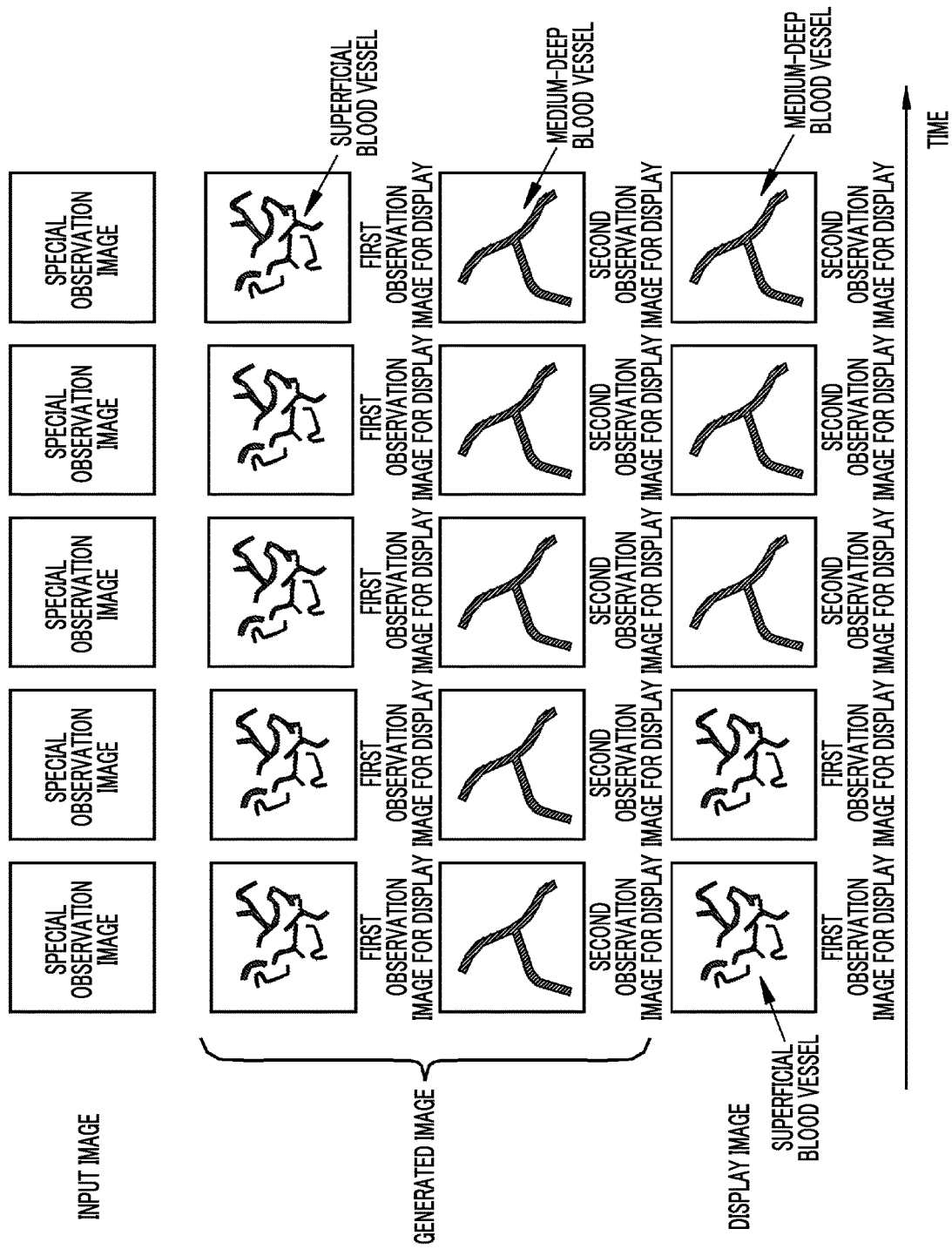
FIG. 6B is a diagram illustrating that both a first observation image for display and a second observation image for display are generated from a special observation image of one frame and any one of the generated observation images for display is displayed.

As another pattern, as shown in FIG. 6B, in a case where special observation images of two frames are input to the multi-observation image processing unit 64 as input images, the multi-observation image processing unit 64 generates first and second observation images for display for two frames as generated images. Among the generated first and second observation images for display for two frames, the first observation images for display for two frames are sequentially displayed on the monitor 18 as display images. After that, in a case where special observation images of three frames are input to the multi-observation image processing unit 64 as input images, the multi-observation image processing unit 64 generates first and second observation images for display for three frames as generated images. Among the generated first and second observation images for display for three frames, the second observation images for display for three frames are sequentially displayed on the monitor 18 as display images. In a case where the storage of the static images of the observation images for display is instructed by a user in the above-mentioned case, the first observation image for display and the second observation image for display are generated from a single frame and are stored. Accordingly, an image in which a deviation in position does not occur in the first observation image for display and the second observation image for display can be stored by a single operation.

It is preferable that the first and second observation images for display are displayed while being switched at an interval of two or more frames. Since the images are quickly switched in a case where the first and second observation images for display are switched at an interval of one frame, there is a concern that a user cannot recognize a difference between the first and second observation images for display.

Next, the image processing for the multi-observation mode will be described. The image processing for the multi-observation mode includes first-observation-image-for-display generation processing for generating the first observation image for display and second-observation-image-for-display generation processing for generating the second observation image for display. As shown in FIG. 7, in the first-observation-image-for-display generation processing, brightness-color difference signal conversion processing is performed on the Bs-image signals, the Gs-image signals, and the Rs-image signals obtained in the multi-observation mode to convert the Bs-image signals, the Gs-image signals, and the Rs-image signals into brightness signals Y and color difference signals Cr and Cb. Then, brightness signal assignment processing for assigning (i.e., replacing) the Bs-image signals (first color signals (blue color signals) of the observation image) to the brightness signals Y is performed to convert the brightness signals Y into brightness signals Ym. That is, the Bs-image signals correspond to first color signals (e.g., blue color signals) of the observation image. Since the B s-image signals include information about superficial blood vessels as described later, the first observation image for display can be used as an image in which superficial blood vessels are emphasized.

Next, color difference signal correction processing for correcting the deviations of the color difference signals Cr and Cb, which are caused by the conversion of the brightness signals Y into the brightness signals Ym, is performed. Specifically, the color difference signals Cr are multiplied by the converted brightness signals Ym/the converted brightness signals Y. Likewise, the color difference signals Cb are multiplied by the converted brightness signals Ym/the converted brightness signals Y. Accordingly, since the deviations of the color difference signals Cr and Cb are corrected, a deviation in saturation can be corrected according to the conversion of brightness while a hue is maintained (a saturation can be reduced in a case where brightness is reduced and a saturation can be increased in a case where brightness is increased). Then, RGB conversion processing is performed on the brightness signals Ym, the color difference signals Cr×Ym/Y, and the color difference signals Cb×Ym/Y, so that the brightness signals Ym, the color difference signals Cr×Ym/Y, and the color difference signals Cb×Ym/Y are converted into B1-image signals, G1-image signals, and R1-image signals. The B1-image signals, the G1-image signals, and the R1-image signals form the first observation image for display.

Figure 8:
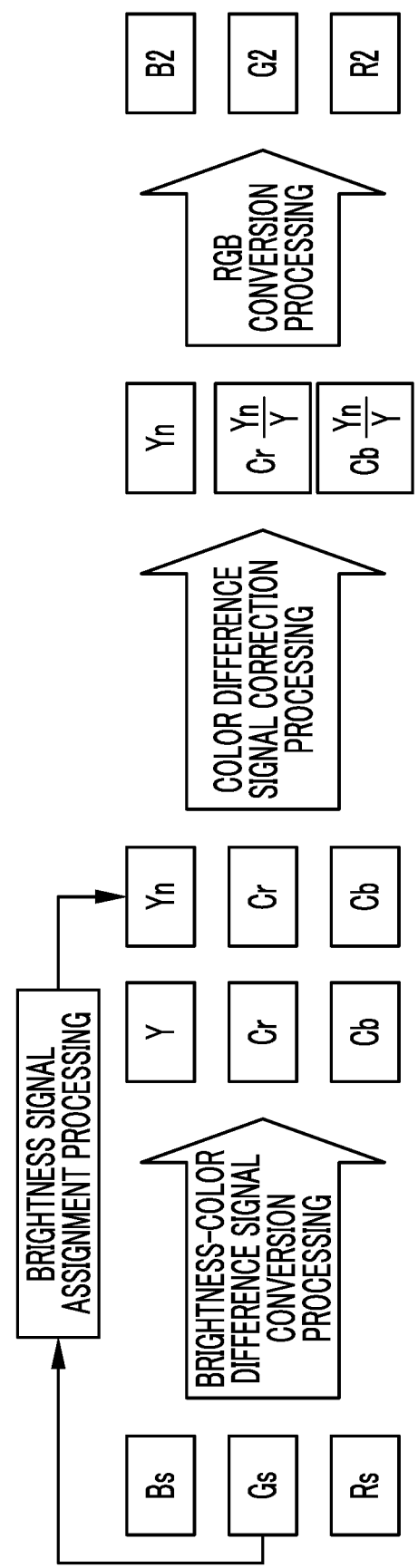
FIG. 8 is a diagram illustrating second-observation-image-for-display generation processing.

As shown in FIG. 8, in the second-observation-image-for-display generation processing, as in the first-observation-image-for-display generation processing, brightness-color difference signal conversion processing is performed on the Bs-image signals, the Gs-image signals, and the Rs-image signals obtained in the multi-observation mode to convert the Bs-image signals, the Gs-image signals, and the Rs-image signals into brightness signals Y and color difference signals Cr and Cb. Then, brightness signal assignment processing for assigning the brightness signals Y to the Gs-image signals (second color signals (green color signals) of the observation image) is performed to convert the brightness signals Y into brightness signals Yn. Since the Gs-image signals include information about medium-deep blood vessels as described later, the second observation image for display can be used as an image in which medium-deep blood vessels are emphasized. The second color signal of the observation image is a color signal that includes a component having a wavelength longer than the wavelength of the first color signal of the observation image. The first color signals are blue color signals and the second color signals are green color signals in this embodiment, but the invention is not limited thereto. For example, the first color signals may be green color signals and the second color signals may be red color signals, such as the Rs-image signals.

Next, color difference signal correction processing for correcting the deviations of the color difference signals Cr and Cb, which are caused by the conversion of the brightness signals Y into the brightness signals Yn, is performed. Specifically, the color difference signals Cr are multiplied by the converted brightness signals Yn/the converted brightness signals Y. Likewise, the color difference signals Cb are multiplied by the converted brightness signals Yn/the converted brightness signals Y. Accordingly, the deviations of the color difference signals Cr and Cb are corrected. RGB conversion processing is performed on the brightness signals Yn, the color difference signals Cr×Yn/Y, and the color difference signals Cb×Yn/Y, so that the brightness signals Yn, the color difference signals Cr×Yn/Y, and the color difference signals Cb×Yn/Y are converted into B2-image signals, G2-image signals, and R2-image signals. The B2-image signals, the G2-image signals, and the R2-image signals form the second observation image for display.

The reason why the Bs-image signals include information about superficial blood vessels and the Gs-image signals include information about medium-deep blood vessels as described above is as follows. As shown in FIG. 9, the Bs-image signal has a signal value corresponding to light intensity that is obtained in a case where the light intensity of the special light, the reflectivity of an object to be observed, and the light transmittance of the B-pixel are multiplied together. The Bs-image signal includes many short-wavelength components of the special light. The Gs-image signal has a signal value corresponding to light intensity that is obtained in a case where the light intensity of the special light, the reflectivity of the object to be observed, and the light transmittance of the G-pixel are multiplied together. The Gs-image signal includes many medium-wavelength components of the special light. The Rs-image signal has a signal value corresponding to light intensity that is obtained in a case where the light intensity of the special light, the reflectivity of the object to be observed, and the light transmittance of the R-pixel are multiplied together. The Rs-image signal includes many long-wavelength components of the special light.

Figure 10:
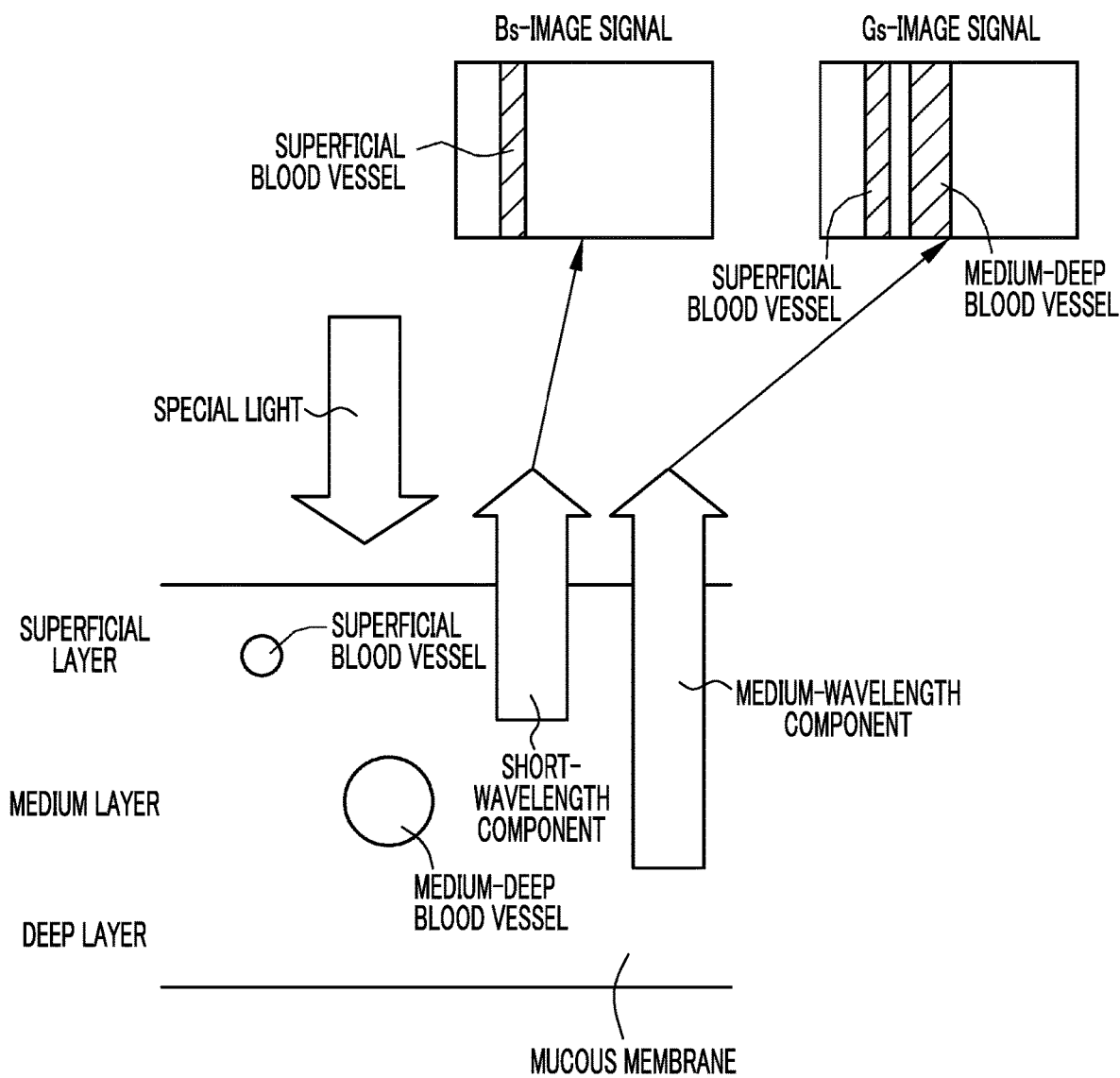
FIG. 10 is a diagram illustrating a relationship between components of the reflected light of special light and a Bs-image signal and a Gs-image signal.

As shown in FIG. 10, many short-wavelength components of the special light included in the Bs-image signal correspond to components of the reflected light of light reaching the surface layer of a mucous membrane. Accordingly, information about superficial blood vessels included in the surface layer of a mucous membrane is included in the Bs-image signal. On the other hand, many medium-wavelength components of the special light included in the Gs-image signal correspond to components of the reflected light of light reaching the vicinity of the middle layer of a mucous membrane. Accordingly, information about superficial blood vessels or medium-deep blood vessels included in the surface layer or the middle layer of a mucous membrane is included in the Gs-image signal. The long-wavelength components of the special light included in the Rs-image signal include information about a mucous membrane other than structures, such as blood vessels. Accordingly, information about a mucous membrane can be displayed by the Rs-image signal.

Figure 11:
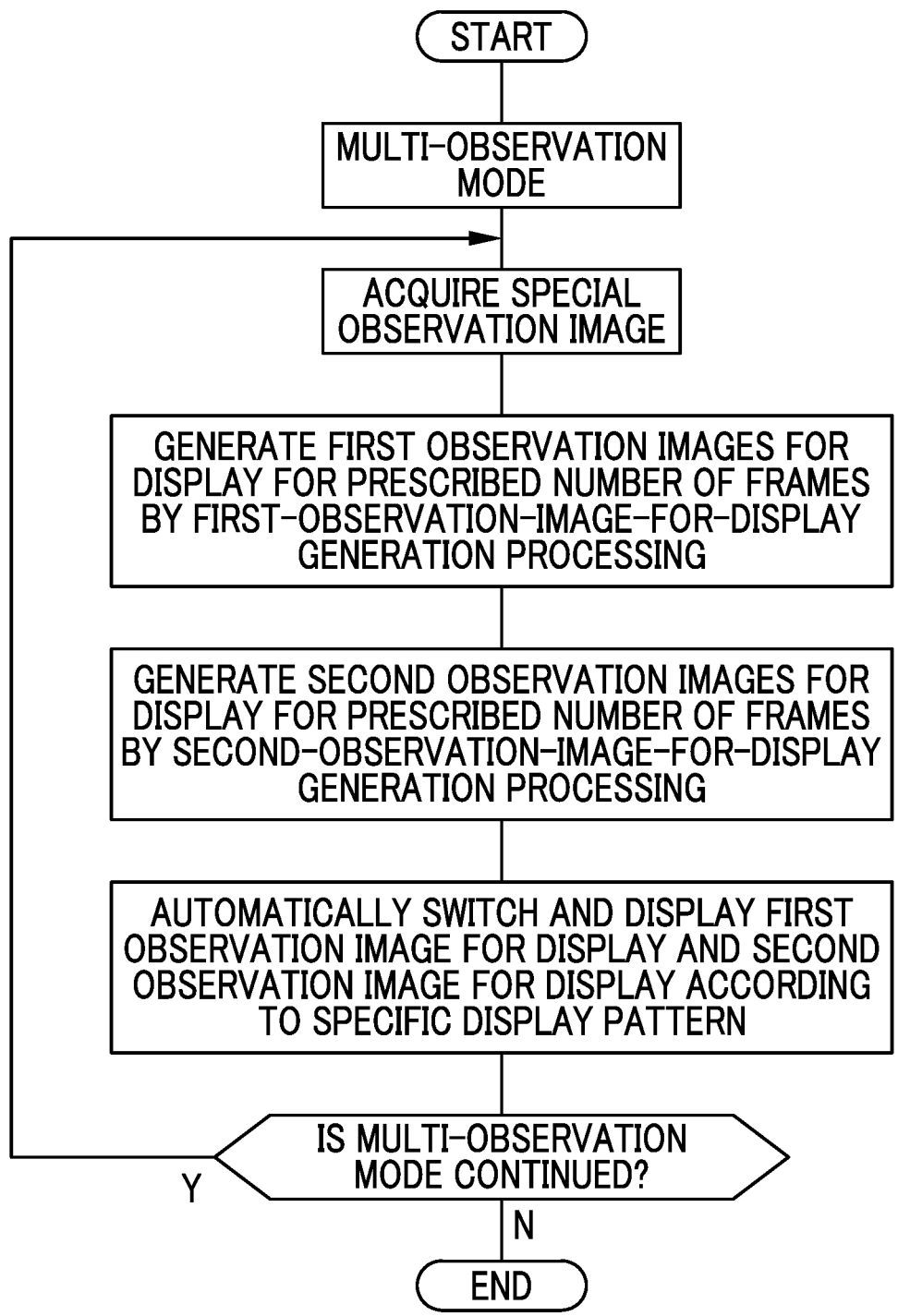
FIG. 11 is a flowchart showing a series of flow of a multi-observation mode.

Next, the multi-observation mode will be described with reference to a flowchart of FIG. 11. A user operates the mode changeover SW 13a to switch a mode to the multi-observation mode. Accordingly, an object to be observed is illuminated with the special light. The image of the object to be observed, which is being illuminated with the special light, is picked up by the image pickup sensor 48, so that a special observation image consisting of the Bs-image signals, the Gs-image signals, and the Rs-image signals is obtained. Next, the first observation images for display for the first prescribed number of frames and the second observation images for display for the second prescribed number of frames are generated from a special observation image of one frame. Here, it is preferable that each of the first prescribed number of frames and the second prescribed number of frames corresponds to the number of frames to be displayed in one display cycle. The first prescribed number of frames and the second prescribed number of frames may be fixed, or may be changed according to a specific condition.

The generation of the first observation images for display is performed by the first-observation-image-for-display generation processing. The brightness signal assignment processing for assigning the Bs-image signals to the brightness signals Y is performed in the first-observation-image-for-display generation processing. Accordingly, the first observation images for display in which superficial blood vessels are emphasized are obtained. Further, the generation of the second observation images for display is performed by the second-observation-image-for-display generation processing. The brightness signal assignment processing for assigning the Gs-image signals to the brightness signals Y is performed in the second-observation-image-for-display generation processing. Accordingly, the second observation images for display in which medium-deep blood vessels are emphasized are obtained. Then, the first observation image for display and the second observation image for display are automatically switched and displayed on the monitor 18 according to a specific display pattern. As long as the multi-observation mode is continued, the above-mentioned processing is repeatedly performed. The brightness signal assignment processing for assigning the Bs-image signals, which include information about superficial blood vessels, to the brightness signals Y and assigning the Gs-image signals, which include information about medium-deep blood vessels, to the brightness signals has a load of image processing smaller than that of processing for emphasizing superficial blood vessels by pattern matching. Accordingly, it is possible to switch the image of superficial blood vessels (first observation image for display) and the image of medium-deep blood vessels (second observation image for display) without applying a load to image processing and the like.

Figure 12:
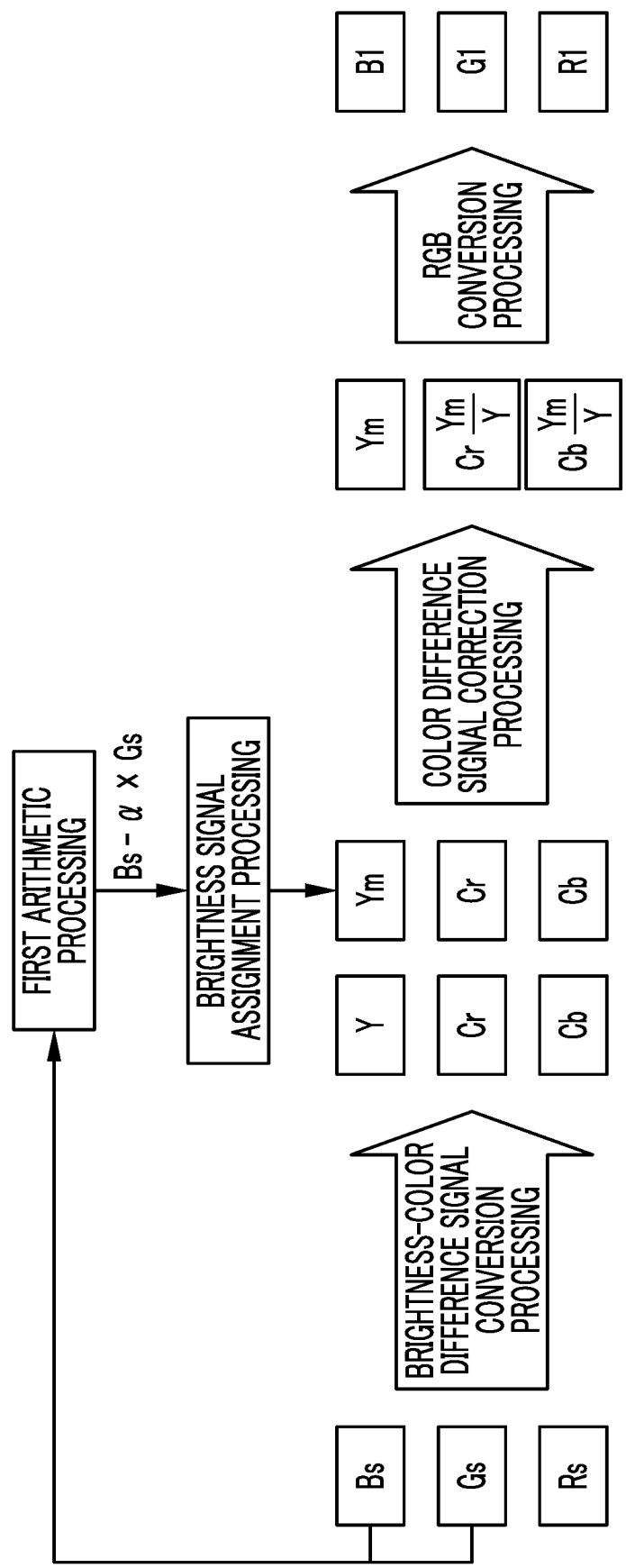
FIG. 12 is a diagram illustrating first-observation-image-for-display generation processing in a case where first arithmetic processing is performed.
Figure 13:
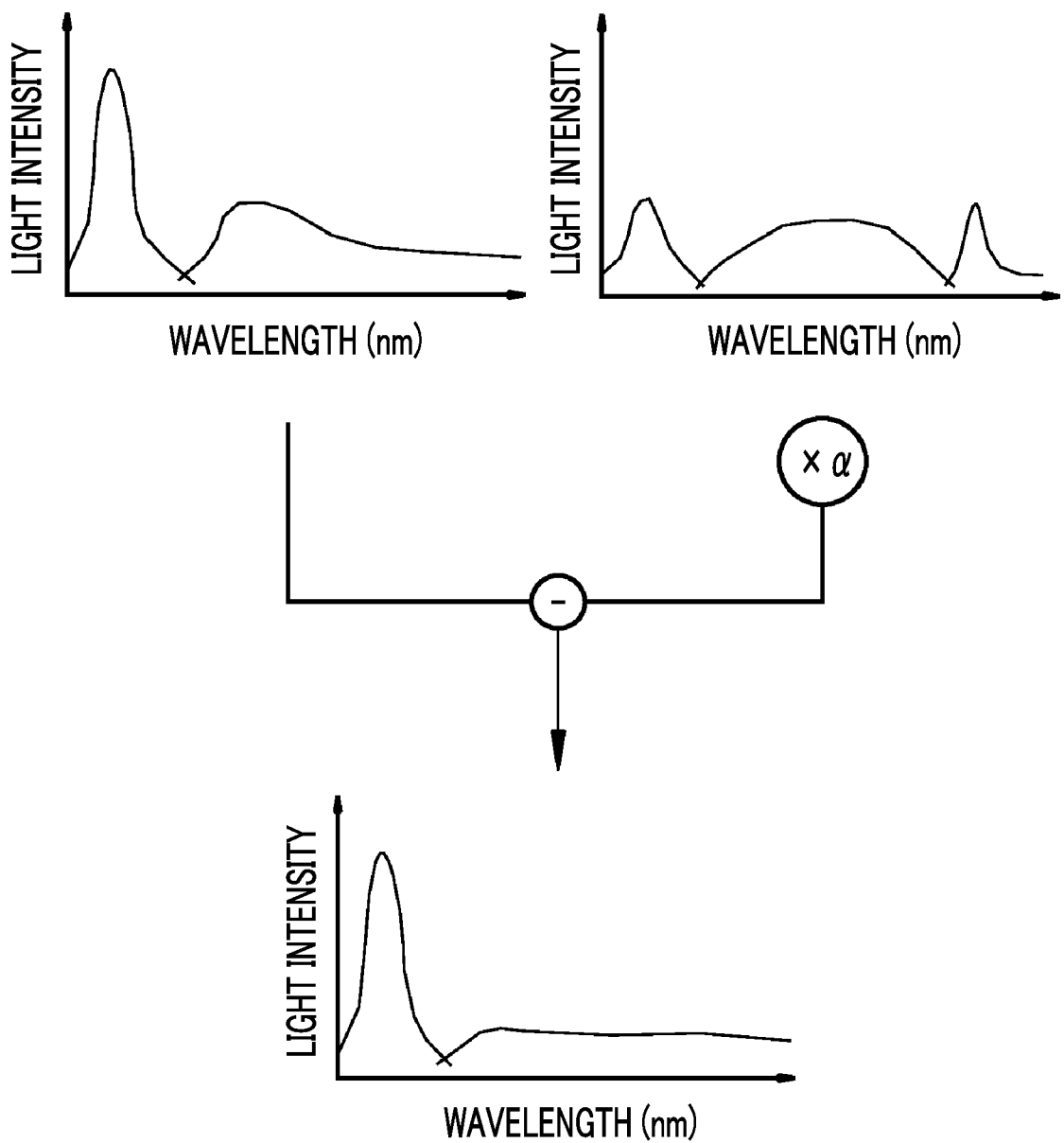
FIG. 13 is a diagram illustrating the first arithmetic processing.

Since the sensitivity characteristics of the B-pixel of the image pickup sensor 48 and the sensitivity characteristics of the G-pixel of the image pickup sensor 48 partially overlap with each other as shown in the embodiment, a difference between the Bs-image signal and the Gs-image signal may be small. In this case, a difference between the first and second observation images for display may be reduced. First arithmetic processing (Bs-α×Gs) for subtracting the Gs-image signal, which is multiplied by a coefficient α, from the Bs-image signal as shown in FIG. 12 is performed as one of methods of reducing a difference between the first and second observation images for display. Accordingly, the medium-wavelength components of the Gs-image signal (components of the second color signal (green color signal) of the observation image) can be removed from the Bs-image signal as shown in FIG. 13. Therefore, since information about medium-deep blood vessels is reduced from the (Bs-α×Gs) image signal, a difference between a first observation image for display in which the (Bs-α×Gs) image signals are assigned to the brightness signals Y and the second observation image for display can be increased.

Further, second arithmetic processing (Gs-β×Bs) for subtracting the Bs-image signal, which is multiplied by a coefficient β, from the Gs-image signal may be performed. Accordingly, the short-wavelength components of the Bs-image signal (components of the first color signal (blue color signal) of the observation image) can be removed from the Gs-image signal. Therefore, a difference between a second observation image for display in which the (Gs-β×Bs) image signals are assigned to the brightness signals Y and the first observation image for display can be increased.

Second Embodiment

In a second embodiment, an object to be observed is illuminated using laser light sources and a fluorescent body instead of the four color LEDs 20a to 20d described in the first embodiment. Others are the same as those of the first embodiment.

Figure 14:
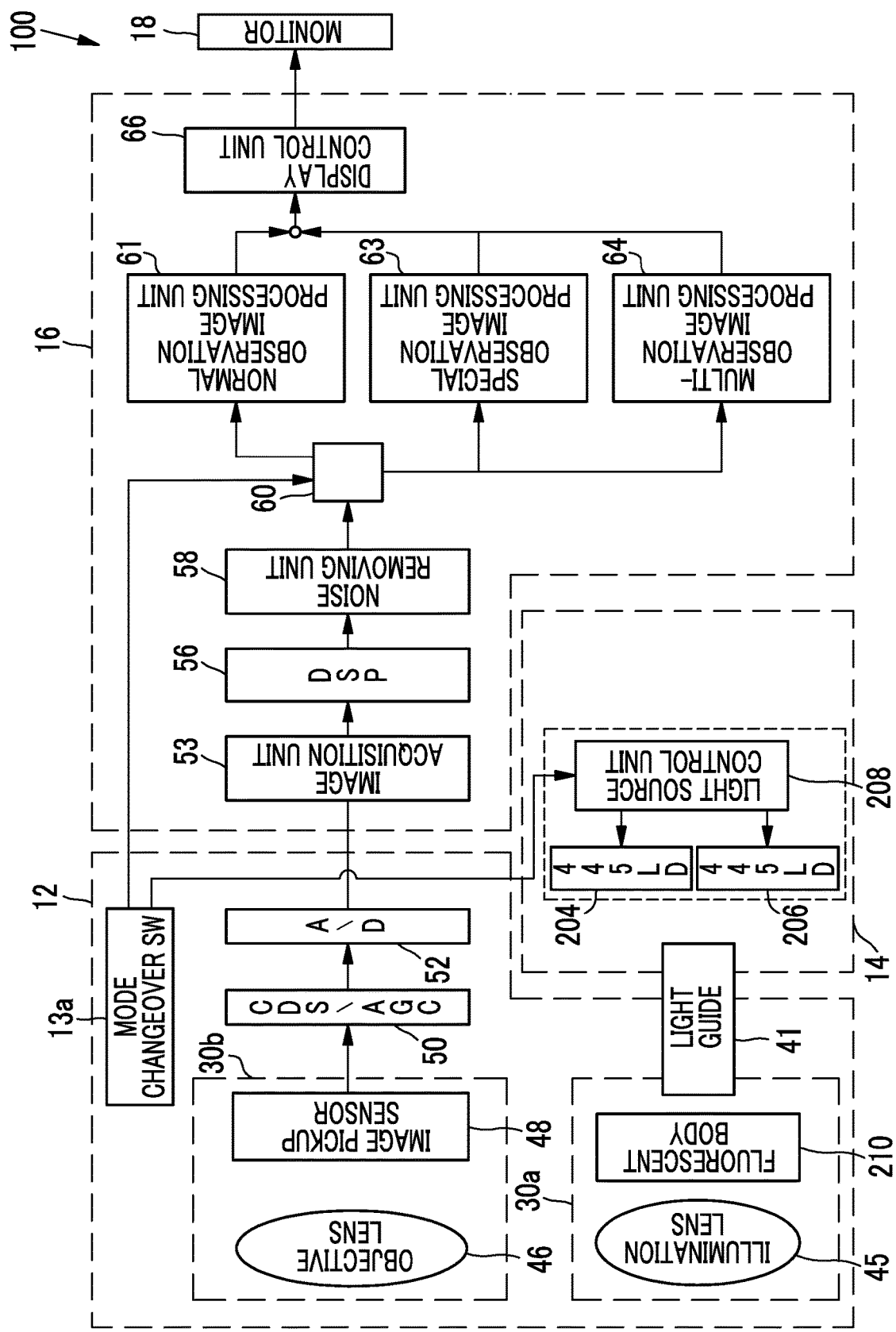
FIG. 14 is a block diagram showing the functions of an endoscope system according to a second embodiment.

As shown in FIG. 14, in an endoscope system 200 according to a second embodiment, a light source device 14 is provided with a blue laser light source (written in FIG. 14 as "445LD") 204 emitting blue laser light of which the central wavelength is in the range of 445±10 nm and a blue-violet laser light source (written in FIG. 14 as "405LD") 206 emitting blue-violet laser light of which the central wavelength is in the range of 405±10 nm, instead of the four color LEDs 20a to 20d. Since the emission of light from semiconductor light-emitting elements of the respective light sources 204 and 206 is individually controlled by a light source control unit 208, a ratio of the amount of light emitted from the blue laser light source 204 to the amount of light emitted from the blue-violet laser light source 206 can be freely changed.

The light source control unit 208 drives the blue laser light source 204 in a normal light observation mode. In a special light observation mode or a multi-observation mode, the light source control unit 208 drives both the blue laser light source 204 and the blue-violet laser light source 206 and controls blue-violet laser light and blue laser light so that the light emission ratio of blue-violet laser light is higher than the light intensity ratio of blue laser light. Laser light emitted from each of the light sources 204 and 206 is incident on the light guide 41 through optical members (all of the optical members are not shown), such as a condenser lens, optical fibers, or a multiplexer.

It is preferable that the half-width of blue laser light or blue-violet laser light is set to about ±10 nm. Further, broad area-type InGaN-based laser diodes can be used as the blue laser light source 204 and the blue-violet laser light source 206, and InGaNAs-based laser diodes or GaNAs-based laser diodes can also be used. Furthermore, a light emitter, such as a light emitting diode, may be used as the light source.

The illumination optical system 30a is provided with a fluorescent body 210 on which blue laser light or blue-violet laser light transmitted from the light guide 41 is to be incident in addition to the illumination lens 45. In a case where the fluorescent body 210 is irradiated with blue laser light, fluorescence is emitted from the fluorescent body 210. Further, a part of blue laser light passes through the fluorescent body 210 as it is. Blue-violet laser light passes through the fluorescent body 210 without exciting the fluorescent body 210. The inside of an object to be examined is irradiated with light, which is emitted from the fluorescent body 210, through the illumination lens 45.

Figure 15:
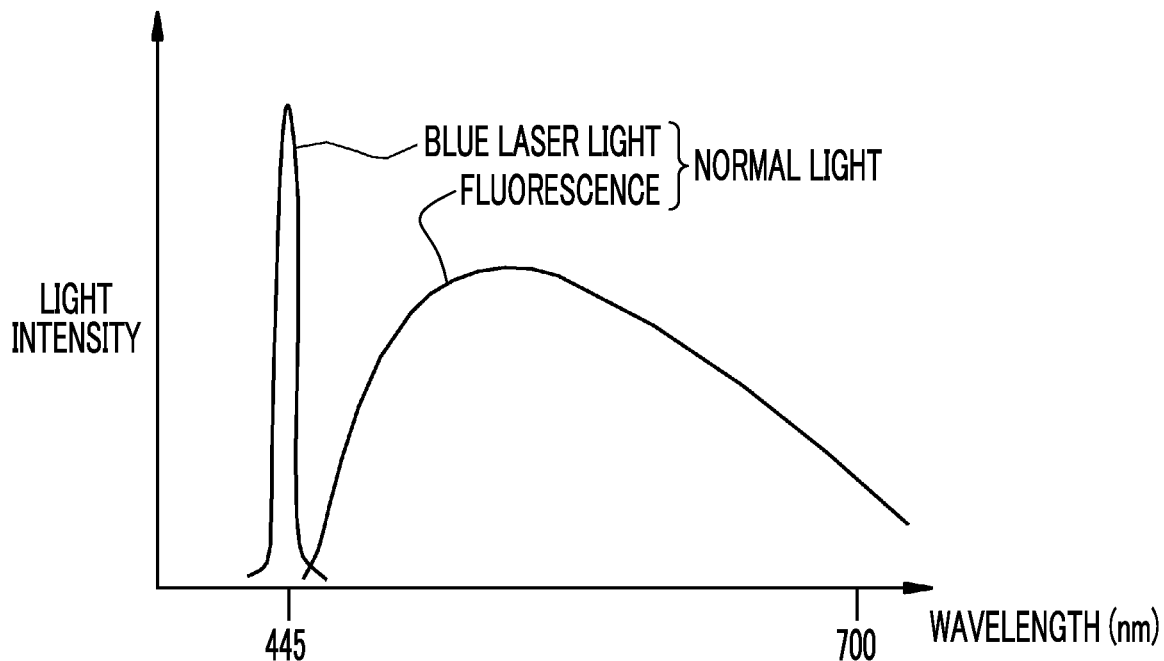
FIG. 15 is a graph showing the emission spectrum of normal light of the second embodiment.
Figure 16:
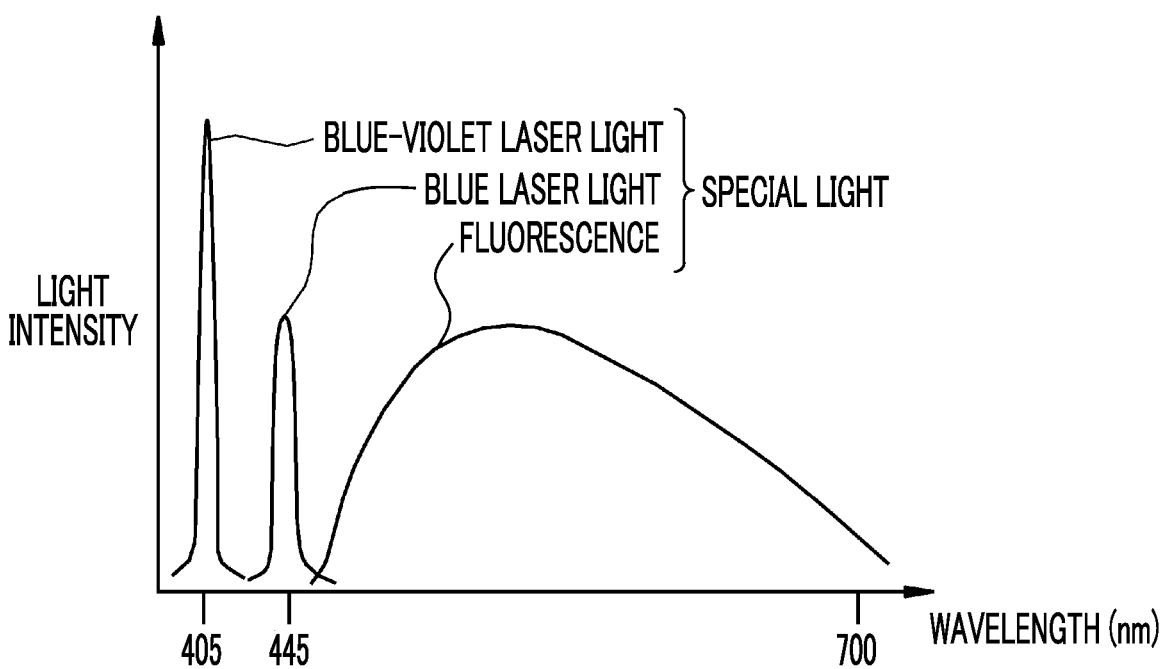
FIG. 16 is a graph showing the emission spectrum of special light of the second embodiment.

Here, since blue laser light is mainly incident on the fluorescent body 210 in the normal light observation mode, an object to be observed is irradiated with normal light shown in FIG. 15 in which blue laser light and fluorescence excited and emitted from the fluorescent body 210 due to blue laser light are multiplexed. Since both blue-violet laser light and blue laser light are incident on the fluorescent body 210 in the special light observation mode or the multi-observation mode, the inside of an object to be examined is irradiated with special light shown in FIG. 16 in which blue-violet laser light, blue laser light, and fluorescence excited and emitted from the fluorescent body 210 due to blue laser light are multiplexed. In the special light, the light intensity of blue-violet laser light is higher than the light intensity of blue laser light.

It is preferable that a fluorescent body including plural kinds of fluorescent bodies absorbing a part of blue laser light and exciting and emitting green to yellow light (for example, YAG-based fluorescent bodies or fluorescent bodies, such as BAM (BaMgAl10O17)) is used as the fluorescent body 210. In a case where the semiconductor light-emitting elements are used as the excitation light source of the fluorescent body 210 as in this example of configuration, high-intensity white light is obtained with high luminous efficiency. Accordingly, not only the intensity of white light can be easily adjusted but also a change in the color temperature and chromaticity of white light can be suppressed to be small.

The hardware structures of the processing units, which are included in the processor device 16 in the embodiment, such as the image acquisition unit 53, the DSP 56, the noise removing unit 58, the normal observation image processing unit 61, the special observation image processing unit 63, and the multi-observation image processing unit 64, are various processors to be described below. The various processors include: a central processing unit (CPU) that is a general-purpose processor functioning as various processing units by executing software (program); a programmable logic device (PLD) that is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs or a combination of a CPU and an FPGA). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

The invention can be applied to various medical image processing devices other than the processor device that is to be combined with the endoscope systems described in the first and second embodiments or a capsule endoscope system.

EXPLANATION OF REFERENCES

10: endoscope system
12: endoscope
12a: insertion part
12b: operation part
12c: bendable part
12d: distal end part 12e: angle knob
14: light source device
16: processor device
18: monitor
19: console
20: light source unit
20a: V-LED (Violet Light Emitting Diode)
20b: B-LED (Blue Light Emitting Diode)
20c: G-LED (Green Light Emitting Diode)
20d: R-LED (Red Light Emitting Diode)
21: light source control unit
23: optical path-combination unit
30a: illumination optical system
30b: image pickup optical system
41: light guide
45: illumination lens
46: objective lens
48: image pickup sensor
50: CDS/AGC circuit
53: image acquisition unit
56: DSP (Digital Signal Processor)
58: noise removing unit
60: signal switching unit
61: normal observation image processing unit
63: special observation image processing unit
64: multi-observation image processing unit
66: display control unit
200: endoscope system
204: blue laser light source
206: blue-violet laser light source
208: light source control unit
210: fluorescent body

What is claimed is:

1. An endoscope system comprising:
a processor configured to:
acquire an observation image;
generate a plurality of observation images for display each including a brightness signal on the basis of the observation image, assign a first color signal of the observation image to the brightness signal to generate a plurality of first observation images for display, and assign a second color signal of the observation image to the brightness signal to generate a plurality of second observation images for display; and
cause a display to automatically switch and display the first observation images for display and the second observation images for display according to a specific display pattern,
wherein the processor is further configured to:
generate, from one frame of the observation image, a first prescribed number of frames of the first observation images for display and a second prescribed number of frames of the second observation images for display, corresponding to the specific display pattern, and
automatically switch, in one display cycle, displaying the first prescribed number of frames of the first observation images for display continuously on the display, and displaying the second prescribed number of frames of the second observation images for display continuously on the display.

2. The endoscope system according to claim 1,
wherein the processor is configured to remove a component of the second color signal of the observation image from the first color signal of the observation image by first arithmetic processing, and
the processor is configured to assign the first color signal of the observation image, which has been subjected to the first arithmetic processing, to the brightness signal to generate the first observation image for display.

3. The endoscope system according to claim 1,
wherein the processor is configured to remove a component of the second color signal of the observation image from the first color signal of the observation image by first arithmetic processing, and
the processor is configured to assign the second color signal of the observation image, which has been subjected to the second arithmetic processing, to the brightness signal to generate the second observation image for display.

4. The endoscope system according to claim 2,
wherein the processor is configured to remove a component of the second color signal of the observation image from the first color signal of the observation image by first arithmetic processing, and
the processor is configured to assign the second color signal of the observation image, which has been subjected to the second arithmetic processing, to the brightness signal to generate the second observation image for display.

5. The endoscope system according to claim 1,
wherein the observation image is a special observation image that is obtained from image pickup of an object to be observed illuminated with special light including blue light or violet light of which a wavelength range is narrowed, green light, and red light.

6. The endoscope system according to claim 2,
wherein the observation image is a special observation image that is obtained from image pickup of an object to be observed illuminated with special light including blue light or violet light of which a wavelength range is narrowed, green light, and red light.

7. The endoscope system according to claim 3,
wherein the observation image is a special observation image that is obtained from image pickup of an object to be observed illuminated with special light including blue light or violet light of which a wavelength range is narrowed, green light, and red light.

8. The endoscope system according to claim 5,
wherein the violet light has a central wavelength in a range of 405±10 nm.

9. The endoscope system according to claim 1,
wherein the first color signal is a blue color signal and the second color signal is a green color signal.

10. The endoscope system according to claim 2,
wherein the first color signal is a blue color signal and the second color signal is a green color signal.

11. The endoscope system according to claim 3,
wherein the first color signal is a blue color signal and the second color signal is a green color signal.

12. The endoscope system according to claim 5,
wherein the first color signal is a blue color signal and the second color signal is a green color signal.

13. The endoscope system according to claim 8,
wherein the first color signal is a blue color signal and the second color signal is a green color signal.

14. The endoscope system according to claim 1,
wherein first layer blood vessels are emphasized in the first observation image for display and second layer blood vessels present at a position deeper than the first layer blood vessels are emphasized in the second observation image for display.

15. The endoscope system according to claim 14, wherein the first layer blood vessels are superficial blood vessels and the second layer blood vessels are medium-deep blood vessels.

16. The endoscope system according to claim 1, wherein the processor is configured to cause the first observation image for display and the second observation image for display to be switched at an interval of two or more frames.

17. A method of operating an endoscope system, the method comprising:

causing a processor to acquire an observation image;

causing the processor to generate generate a plurality of observation images for display each including a brightness signal on the basis of the observation image, to assign a first color signal of the observation image to the brightness signal to generate a plurality of first observation images for display, and to assign a second color signal of the observation image to the brightness signal to generate a plurality of second observation images for display; and causing the processor to cause a display to automatically switch and display the first observation images for display and the second observation images for display according to a specific display pattern, wherein the method further comprises:

causing the processor to generate, from one frame of the observation image, a first prescribed number of frames of the first observation images for display and a second prescribed number of frames of the second observation images for display, corresponding to the specific display pattern, and causing the processor to automatically switch, in one display cycle, displaying the first prescribed number of frames of the first observation images for display continuously on the display, and displaying the second prescribed number of frames of the second observation images for display continuously on the display.

* * * * *